(12) United States Patent
Pagés Pinyol

(10) Patent No.: US 7,511,818 B2
(45) Date of Patent: Mar. 31, 2009

(54) APPARATUS FOR MEASURING THE OPTICAL ABSORBENCY OF SAMPLES OF LIQUIDS, METHOD AND REACTION CONTAINER FOR ITS IMPLEMENTATION

(75) Inventor: Josep Pagés Pinyol, Barcelona (ES)

(73) Assignee: Grifols, S.A., Barcelona (ES)

( * ) Notice: Subject to any disclaimer, the term of this patent is extended or adjusted under 35 U.S.C. 154(b) by 352 days.

(21) Appl. No.: 11/280,546

(22) Filed: Nov. 15, 2005

(65) Prior Publication Data

US 2006/0103846 A1  May 18, 2006

(30) Foreign Application Priority Data

Nov. 18, 2004  (ES) ................................ 200402774

(51) Int. Cl.
*G01N 21/00* (2006.01)

(52) U.S. Cl. ...................................... 356/436; 356/432

(58) Field of Classification Search ....................... None
See application file for complete search history.

(56) References Cited

U.S. PATENT DOCUMENTS

| 5,314,825 A | 5/1994 | Weyrauch et al. |
|---|---|---|
| 2002/0176801 A1 | 11/2002 | Giebeler et al. |

*Primary Examiner*—Gregory J Toatley, Jr.
*Assistant Examiner*—Amanda H Merlino
(74) *Attorney, Agent, or Firm*—Darby & Darby P.C

(57) ABSTRACT

Apparatus for measuring the optical absorbency of samples of liquids, method and reaction container for its implementation.

The apparatus comprises a receiving body for receiving the reaction containers carrying the samples to be analyzed, with means for causing each of the reaction containers to be passed through by a luminous signal of controlled wavelength, having means for conducting it to a scanning head where the luminous signals are picked up by a single CCD sensor, constituting a digital processing system for evaluating the absorbency of the corresponding sample.

12 Claims, 2 Drawing Sheets

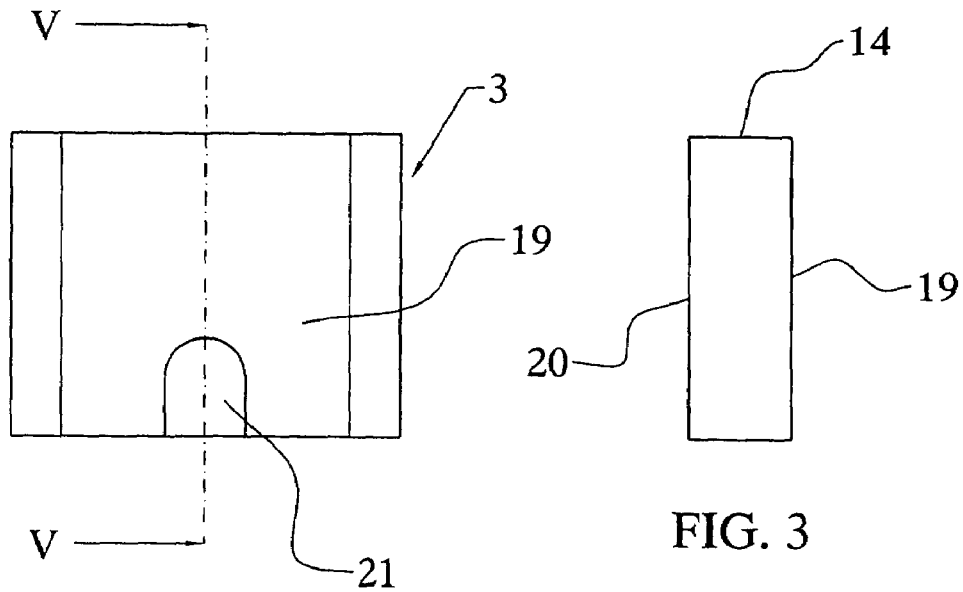
FIG. 2
FIG. 3
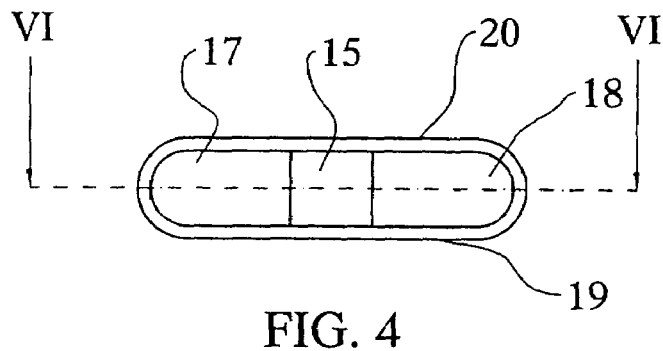
FIG. 4
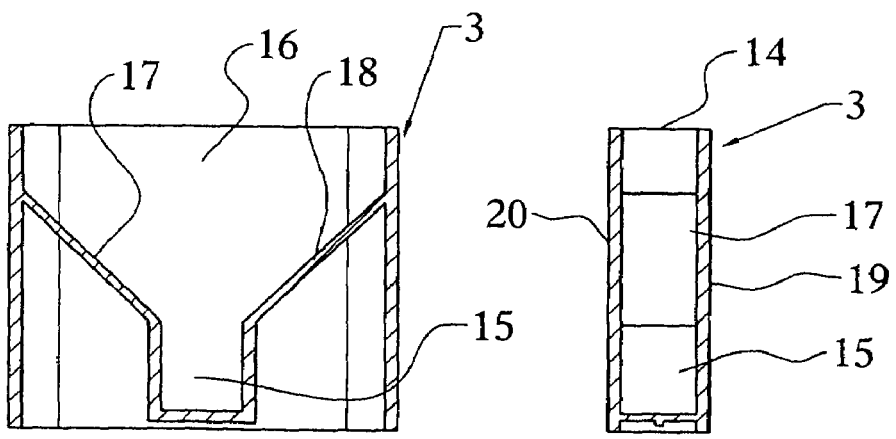
FIG. 5
FIG. 6

APPARATUS FOR MEASURING THE OPTICAL ABSORBENCY OF SAMPLES OF LIQUIDS, METHOD AND REACTION CONTAINER FOR ITS IMPLEMENTATION

DESCRIPTION

The present invention relates to an apparatus intended for obtaining information on the optical absorbency of a liquid after a reaction which has taken place in a reaction container or during the actual reaction. The apparatus is especially suitable for the simultaneous measurement of a series of samples of liquids and for carrying out measurements in which the development over time of the absorbency of a specific sample is studied. The invention likewise relates to a method for carrying out the measurement and a specific reaction container therefor.

The apparatus of the present invention has a body preferably in the shape of an arc of a circle provided with a multiplicity of radially arranged seats, each of which is capable of receiving a reaction container carrying a sample on which measurement is to be carried out. Each of said seats constitutes the entry of a scanning channel and may be in the form of a through channel, so that the reaction containers enter through one end of each channel and exit through the other by means of linear thrust or a similar system. Said body for the reaction containers, depending on the requirements of the measurement to be carried out, may or may not be equipped with thermostatic control means. The radial arrangement of the individual channels for the reaction containers with a certain separation between them makes it possible for the reaction containers to be transferred from and to similar concentric devices when the channels are opposite same, for example, a device containing the empty reaction containers and other devices of the same apparatus that are located concentrically within the body of the scanning device. The upper part of the seats is protected by a lid which may be partially uncovered in order to enable liquids to be added to the reaction container whilst it is in the channel.

The reaction containers which are used in the apparatus have a structure approximately in the shape of a parallelepiped and are provided internally with a small lower cavity for receiving a part of the sample and of the reagents, and which is the part where the reactions take place and the absorbency, or the variation in absorbency of which is to be measured. Said minor cavity, located in the lower part of the reaction container, is provided with transparent windows on both of the principal faces of the reaction container in order to allow optical scanning via an optical path transverse to the reaction container.

In order to carry out the measurements of absorbency, it is possibile to send a luminous signal to each of the scanning channels by means of a preferably single halogen or other type of lamp, connected to an external light control signal, so that in order for it to be focused, the luminous signal will pass through a concentrating lens, there being in addition a motor-driven wheel with a multiplicity of filters, for example seven filters, which makes it possible to select the wavelength of the luminous signal which will pass through the reaction container. The filter selection mechanism is composed of a motor and an external control signal. The concentrating lens will focus the luminous signal onto a bundle of optical fibres which preferably branches into twelve lines, eight of which are those charged with supplying to each scanning channel the beam of light which passes through the reaction container, and the other four are intended for reference signals.

In order to reduce to a minimum the space between the channels of the body of the apparatus, the individual optical fibres, both those which carry the signal to the reaction container and those which pick up the signal transmitted, are placed in an arrangement parallel in the same direction, which requires a change of 90° at the entry and the exit of each channel, so that the course of the light is correct. Said change of course is implemented by means of pairs of prisms. A pair of lenses located at each end of the reaction container, with a suitable focal length, make it possible to focus the light in parallel through the reaction container, maximising the amount of light which proceeds from one fibre, passes through the reaction container and is picked up in another outgoing fibre. Preferably, the optical prism assembly which is repeated on each of the scanning channels may be constructed in one piece which, for the sake of simplicity, will be designated in this description as "periscope".

The eight fibres which pick up the light from each scanning channel will stop at a scanning head which is a support intended to position the optical fibres so that the light which emerges from each one can be picked up by an image-taking camera. The scanning head is also reached by four optical fibres which proceed from the bundle of optical fibres and which have passed respectively through different grey filters having absorbencies distributed in the dynamic scanning range and which act as references. The purpose of these references is to correct small variations in intensity of the light source over time (drifts of the light source). The signal obtained on each of the eight channels must be corrected with a variation which is observed in comparison with the references, one being selected in dependence on the most convenient signal level.

A CCD sensor or the like is intended for scanning in the head, being equipped with its corresponding optical device and containing the sensor, and also incorporating an analog-to-digital (A/D) converter, the processor and a communication system which allow the luminous signal obtained from the scanning head to be processed with the object of quantifying the absorbency of the corresponding scanning channel.

The twelve individual fibres which enter the scanning head, that is, eight for the entry of the signal into the channels and four for reference, are arranged in a very specific manner, dividing the head into twelve notional lines and twelve notional columns and arranging the fibres so that their points of arrival at the head do not coincide with any other either in line or in column, and in addition maximising the mutual distances between said points, with the object of reducing to a minimum the signal interference effect or "cross-talk" effect which tends to occur in the sensors, given the interference between elements of the same lines or columns of the matrix of photo-detectors. In accordance with this arrangement, in each line and column of the matrix of the CCD camera, there is information on only one of the fibres, thereby minimising the effect of interference.

In order to determine the absorbency of the liquid contained in the corresponding reaction container, the processing takes place automatically, by means of suitable software, of the image of the scanning head picked up by the sensor, which takes successive shots of the scanning head with a specific time interval, for example 40 ms. Each of said shots is taken with a different acquisition time (which will also be currently designated as "shutter") which may belong for example to a sequence of five shutters, of 20,000, 8,000, 4,000, 1,000 and 100 µs, which take turns cyclically and which are controlled by an external control system. The long exposures are suitable for detecting weak signals and the short ones are suitable for strong signals. An analysis is made of the intensities picked up by the photo-detector elements of the camera or pixels which correspond to specific predetermined windows which coincide with the positions of fibres in the scanning head. The acquisition time selected for measurement, beginning with the longest, is the first which does not cause saturation in any pixel.

The intensity of a scanning channel is taken as the arithmetic mean of the pixels of its corresponding window. Said intensity (correcting the drift due to the light source by means of comparison with one of the four reference channels) is compared with that obtained previously for a reaction container with water, and the absorbency of the liquid sample analyzed is obtained.

The measurement of the luminous intensity of a channel as the average of a window of pixels of the sensor not only makes it possible to reduce noise, but also provides advantages of resolution. Although all the pixels of the window corresponding to a channel measure the same luminous signal, the noise and small variations in sensitivity that are present will have the effect that not all of them pick up the same intensity value, but small variations around a certain intensity. These small variations affect the numerical value of the average, so that although the resolution of a photo-detector element of the sensor is usually 256 discrete levels of intensity, the fact of averaging different intensities will make it possible to obtain a specific decimal accuracy which allows the resolution to be increased. For example, if the window of a channel is of 100 pixels and the level of measurement of each pixel passes from 167 to 168, the small variations will have the effect that the sum of all of them does not pass suddenly from 167.00 to 168.00, but will do so gradually, and therefore an average between said values is obtained, which will make it possible to gain two decimals of resolution. Statistically, it would be possible, in dependence on the noise and owing to its presence, to calculate what is the real improvement that can be obtained.

One of the new characteristics of the present invention lies in the use of a single sensor for measuring a multiplicity of optical absorbencies simultaneously. The advantage which this provides lies in requiring only one sensor for all the channels and also in avoiding the expensive systems for amplifying the signal that would be necessary if using photodiodes or photomultipliers. The problem of the dynamic range of this type of sensor tending to be limited compared with photodiodes or photomultipliers has been solved by means of the control of the acquisition time or "shutter", so that the combination of different acquisition times makes it possible to define a plurality of scales of measurement which, overlapped, cover a wide dynamic range. In addition, the use of reference channels renders the system independent of variations in the power of the light source.

The presence of the so-called "periscopes" allows the entry and exit of the optical fibres to be effected through the same end of the scanning zone, thus advantageously minimising the space required.

For greater understanding thereof, by way of non-limiting example, some drawings of an apparatus for measuring absorbency according to the present invention are appended.

FIGS. 2 to 6 show different views, both in dihedral, front elevation, side and plan views, and also views in section along the section planes indicated, of a reaction container used for the implementation of the present invention.

Figure 1:
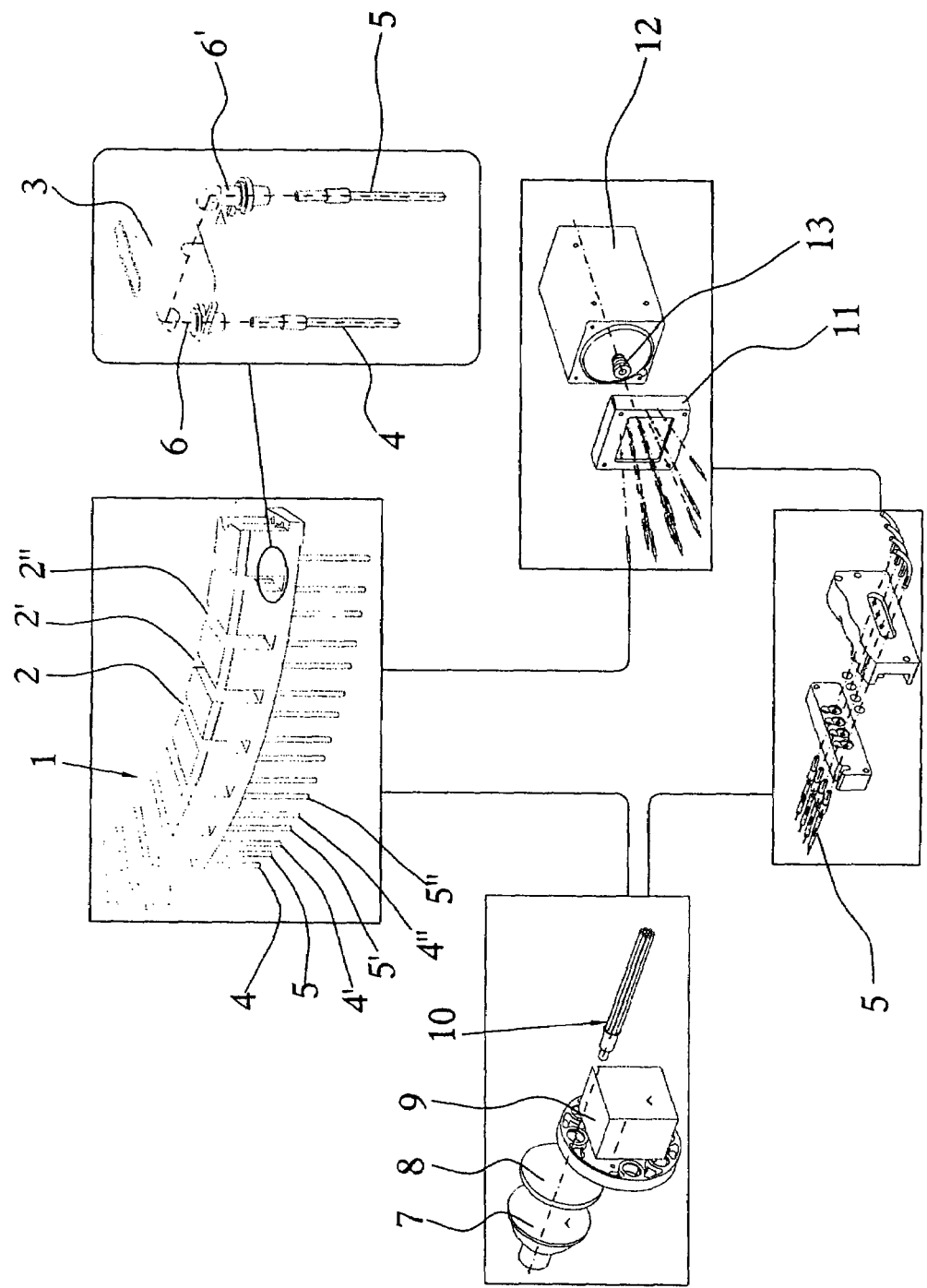
FIG. 1 shows diagrammatically and with elements in perspective, a representation of the different blocks making up the scanning apparatus.

The apparatus of the present invention comprises firstly a body 1, of generally arcuate structure, and provided with a multiplicity of seats such as the grooves 2, 2', 2", arranged radially with a certain separation between them. Each of said seats is the entry of a scanning channel and permits the seating of a reaction container such as those shown in FIGS. 2 to 6, which will be explained in greater detail hereinafter. The arcuate construction with radial grooves permits the combination of the body of the scanning device with other elements of the apparatus that are intended for scanning or for the entry and exit of the reaction containers and other like elements. The execution of the simple straight grooves as a seat for the reaction containers allows their easy introduction and extraction by simple linear thrust.

A luminous signal reaches each of the grooves 2, 2', 2" via a corresponding optical fibre, said luminous signal passing through the corresponding reaction container 3 and returning via another optical fibre. This has been represented diagrammatically in FIG. 1, in which can be seen the optical fibres 4 and 5 for the reaction container 3, it being understood that said arrangement of two optical fibres is repeated for each of the grooves, there being shown in the same FIG. 1, associated with the body 1, a multiplicity of optical fibres such as 4, 4', 4" for one of the sides of the reaction containers and 5, 5', 5" for the opposite sides. The arrangement of the optical fibres in parallel makes it possible to keep the space between channels to a minimum. However, it requires a change of direction of 90° for the light beam at the entry and exit of each channel, for which purpose respective elements of optical prisms and individual lenses are provided in opposition on both sides of each channel, two of which have been shown by way of example with the numbers 6 and 6' in FIG. 1. Said devices are also currently known by the designation of "periscopes".

The luminous signal which reaches each of the scanning channels comes from a single halogen or other type of lamp 7, FIG. 1, connected to an external light control signal. In order for it to be focused, the luminous signal passes through a concentrating lens 8, and a motor-driven wheel having a multiplicity of filters, for example seven filters, makes it possible to select the wavelength of the luminous signal which will pass through the reaction container. The filter selection mechanism is composed of a motor 9 and an external control signal. The concentrating lens 8 focuses the luminous signal onto a bundle of optical fibres 10 which branches into twelve lines, eight of which are those charged with supplying to each scanning channel a light beam which passes through the corresponding reaction container.

The eight fibres which pick up the light from each scanning channel will stop at the scanning head 11, FIG. 1, which is a support intended to position the optical fibres so that the light which emerges from each one can be picked up by an image-taking camera. The scanning head 11 is also reached by four optical fibres which proceed from the bundle of optical fibres 10 and which have passed respectively through different grey filters having absorbencies distributed in the dynamic scanning range and which act as reference. The purpose of the references mentioned is to correct small variations in intensity of the light source over time (drifts of the light source), so that the signal obtained on each of the eight channels must be corrected with the variation which is observed in the references, one being selected in dependence on the most convenient signal level.

The scanning head 11 is read by a CCD sensor or the like 12, FIG. 1, with its corresponding optical system 13. The device which contains the sensor 12 also incorporates the analog-to-digital converter, the processor and the communication system which allow the luminous signal obtained from the scanning head 11 to be processed in order to quantify the absorbency of each of the scanning channels.

The twelve individual fibres which enter the scanning head 11 are arranged in a specific manner according to which said head 11 is divided into twelve notional lines and twelve notional columns and the fibres are arranged so that their points of arrival at the head 11 do not coincide with any other either in line or in column, and in addition the distances between said points are maximised. The object of this arrangement is to reduce to a minimum the interference effect which tends to occur in the sensors between elements of the same lines or columns of the matrix of photo-detectors. In accordance with this arrangement, in each line and column of the matrix of the sensor camera 12, there is information on only one of the fibres, thereby minimising the effect of interference.

In order to determine the absorbency of the liquid which the reaction container 3 contains, the processing takes place automatically, by means of suitable software, of the image picked up by the scanning head 11 produced by the sensor 12. Said sensor 12 takes shots of the scanning head 11 at specific time intervals, for example 40 ms. Each of these shots is taken with a different acquisition time or shutter which belongs to a sequence of five acquisition time periods or shutters, of 20,000, 8,000, 4,000, 1,000 and 100 µs, which take turns cyclically, directed by an external control system. The long exposures will be suitable for detecting weak signals and the short ones for strong signals. An analysis will be made of the signals picked up by the photo-detector elements of the camera or pixels which correspond to specific predetermined windows which coincide with the positions of the fibres in the scanning head. The acquisition time selected for measurement, beginning with the longest, is the first which does not cause saturation in any pixel.

The intensity of a scanning channel is taken as the arithmetic mean of the pixels of its corresponding window. Said intensity, once the drift due to the light source is corrected by means of comparison with one of the four reference channels, is compared with that obtained previously for the reaction container with water, and the absorbency of the liquid analyzed is obtained.

The measurement of the luminous intensity of a channel as the average of a window of pixels of the sensor not only makes it possible to reduce noise, but also provides advantages with regard to resolution.

Even when all the pixels of the window which correspond to a channel measure the same luminous signal, the noise and small variations in sensitivity that are present will have the effect that not all of them pick up the same intensity value, but small variations around a certain intensity which affect the numerical value of the average, which makes it possible to obtain a certain decimal accuracy which increases the resolution.

When the sequence of five shutters is repeated, a measurement of absorption is available every 0.2 seconds. The system is suitable for reactions in which it is of interest to know the absorbency as a function of time, for example, measurements of coagulation without ruling out final point measurements. Although the scanning of the head is continuous, only the absorbency of channels where there is a reaction container is measured, so that the measurement of each channel starts when a trigger fires, and ends after a predetermined time.

The system of scanning with camera which has been described can be used as a conventional photometer in apparatus in which microchips are processed on which a photometric reaction is produced in each well and which, therefore, currently take a conventional photometer. The substitution of the conventional photometer by the system with camera which has been described makes it possible to obtain similar performances but at the same time it is possible to take readings of other types of reactions for the scanning of which it is currently necessary to have recourse to image processing. Therefore, by means of the present invention it is possible to obtain what could be designated as a dual device or system of photometric and image scanning that is autonomous or incorporated as part of an item of equipment, for example, the apparatus of the present invention, in which readings of both types can be taken irrespectively.

The reaction containers 3 have been shown in detail in FIGS. 2 to 6. Their structure is substantially that of a parallelepiped, open at the top 14, and they have internally a lower cavity 15 of smaller capacity, preferably joined to the upper chamber 16 of the reaction container by means of inclined walls such as 17 and 18 which permit the easy arrival of the liquid of the sample and/or reagents in the lower measuring chamber 15. Said lower measuring chamber 15 is intended to receive the optical signal and to allow it to be picked up at the exit, for which purpose the major faces 19 and 20 have respective windows frontally limiting the chamber 15, of which the window 21 has been shown in FIG. 2. Said windows are made of a transparent material in order to allow the passage of the luminous signal.

Although the invention has been explained and described on the basis of a preferred embodiment, it should be understood that it will not be limited to the example described, it being possible to include therein all those variations which may be deduced by an expert in the field after studying the present description, claims and drawings, provided that they come within the scope of the following claims.

The invention claimed is:

1. A method for measuring optical absorbency of samples, comprising the steps of:
   (a) obtaining one or more samples;
   (b) individually placing each sample into a separate reaction container, wherein each reaction container has two windows frontally limiting the chamber;
   (c) passing a luminous signal through the sample and the window and into a sample optical fiber corresponding to each container;
   (d) directing the sample optical fibers through a scanning head that supports and positions the fibers; wherein the scanning head defines a matrix of lines and columns, wherein the point of arrival of each sample optical fiber does not coincide with the point of arrival of any other sample optical fiber in line or column, and the distance between the sample optical fibers is maximized;
   (e) using a single sensor to simultaneously measure optical intensities of the luminous signals emitted from each sample optical fiber exiting the scanning head; and
   (f) calculating optical absorbency of each sample using the measured intensities.

2. The method of claim 1 wherein the optical intensities are measured at the scanning head at time points separated by a predefined fixed time.

3. The method of claim 1, wherein the optical intensities are measured at the scanning head using different acquisition times directed by an external control system.

4. The method of claim 3 wherein the acquisition times selected are the ones that do not cause saturation at the sensor.

5. The method of claim 1, wherein the sensor comprises pixels corresponding to the points in the matrix that coincide with the positions of the luminous signals emitted from each sample optical fiber in the scanning head; and wherein the intensity of each sample optical fiber is measured with a mathematical operation of the pixels intensity corresponding to each point of each acquisition time selected.

6. The method of claim 1, wherein the singe sensor is composed of elements sensitive to light and disposed matricially.

7. The method of claim 3, wherein different periods of acquisition time are combined in order to define a plurality of scales of measurement which, overlapped, cover a wide dynamic range.

8. The method of claim 1, further comprising the step of passing the luminous signal through different grey filters having an absorbency in the dynamic range, and into a reference optical fiber.

9. The method of claim 8, further comprising the step of:
directing the reference optical fibers through a scanning head that supports and positions the fibers;
wherein the scanning head defines a matrix of lines and columns, wherein the point of arrival of each reference optical fiber does not coincide with the point of arrival of any other reference optical fiber in line or column, and the distance between the reference optical fibers is maximized.

10. The method of claim 9, wherein the simultaneously measured intensities comprise the intensity of the sample optical fibers and the intensity of the reference optical fibers for further comparison between them in order to correct the drift in the luminous signal.

11. The method of claim 1, wherein calculation of the optical absorbency comprises comparing the measured intensities to the optical intensity of a control sample having known absorbency.

12. The method of claim 11, wherein the control sample is water.

* * * * *